United States Patent
Kunze et al.

(10) Patent No.: US 12,369,812 B2
(45) Date of Patent: Jul. 29, 2025

(54) DETECTION OF MIS-TRIGGERING IN HEART MRI

(71) Applicant: Siemens Healthineers AG, Erlangen (DE)

(72) Inventors: Karl-Philipp Kunze, London (GB); Radhouene Neji, London (GB)

(73) Assignee: Siemens Healthineers AG, Erlangen (DE)

( * ) Notice: Subject to any disclaimer, the term of this patent is extended or adjusted under 35 U.S.C. 154(b) by 84 days.

(21) Appl. No.: 18/232,440

(22) Filed: Aug. 10, 2023

(65) Prior Publication Data

US 2024/0049976 A1    Feb. 15, 2024

(30) Foreign Application Priority Data

Aug. 12, 2022   (EP) .................................... 22190216

(51) Int. Cl.
*A61B 5/055* (2006.01)
*A61B 5/00* (2006.01)

(52) U.S. Cl.
CPC ............ *A61B 5/055* (2013.01); *A61B 5/0044* (2013.01); *A61B 5/7289* (2013.01); *A61B 5/7425* (2013.01)

(58) Field of Classification Search
CPC ..... A61B 5/055; A61B 5/0044; A61B 5/7289; A61B 5/7425; G01R 33/5673
See application file for complete search history.

(56) References Cited

U.S. PATENT DOCUMENTS 5,000,182 A * 3/1991 Hinks .................... A61B 5/352
                                                          600/509
2022/0349976 A1   11/2022 Kunze et al.

OTHER PUBLICATIONS

Lorenzo Di Sopra et al: "An Automated Approach to Fully Self-Gated Free-Running Cardiac and Respiratory Motion-Resolved 50 Whole-Heart MRI", Magnetic Resonance in Medicine, vol. 82, No. 6, Dec. 2, 2019 (Dec. 2, 2019), pp. 2118-2132, XP055722705.

* cited by examiner

*Primary Examiner* — Jason M Ip
(74) *Attorney, Agent, or Firm* — Banner & Witcoff Ltd.

(57) ABSTRACT

Cardiac MR data sets are acquired over cardiac cycles and based on a trigger event, with each cardiac MR data set having a corresponding time stamp. A series of time differences is determined between acquisitions of the cardiac MR data sets based on the time stamps, and a default time difference representing the time difference between two consecutive cardiac MR data sets is determined, which were acquired using correct trigger events. A pair of incorrect time differences is determined, each incorrect time difference representing a time difference between two consecutive MR data sets in which at least one MR data set was acquired using an incorrect trigger event. Approved MR data sets are determined comprising cardiac MR data sets from the cardiac MR data sets which were acquired using the correct trigger event, based on the pair of incorrect time differences, and the approved MR data sets are further processed.

17 Claims, 3 Drawing Sheets

DETECTION OF MIS-TRIGGERING IN HEART MRI

CROSS-REFERENCE TO RELATED APPLICATIONS

The present application claims priority to and the benefit of Europe patent application no. EP 22190216.6, filed on Aug. 12, 2022, the contents of which are incorporated herein by reference in their entirety.

TECHNICAL FIELD

The present application relates to a method for processing a plurality of cardiac MR data sets, to a processing unit configured to process the plurality of cardiac MR data sets, to a computer program comprising program code, and a carrier comprising the computer program.

BACKGROUND

Dynamic Contrast-Enhanced Magnetic Resonance Imaging (DCE-MRI) captures multiple single-shot images of tissue perfusion after contrast injection, aiming at identifying hypoperfusion in an organ of interest. Key factors for clinical application of dynamic MRI are image resolution and morphologic (slice) coverage, which can usually only be increased when using higher acceleration factors. The use of high acceleration factors (e.g. >3) demands more complex reconstruction frameworks employing regularization through time, making use of data redundancy across the dynamic series. However, regularization methods generally do not perform well in the presence of motion, with the two types of motion commonly encountered being cardiac (contraction of the heart) and respiratory. Additionally, post-processing of reconstructed image data, such as absolute quantification of perfusion, also requires the heart to be in the same motion state across the whole dynamic series.

It is generally assumed that cardiac motion is frozen across the whole dynamic series by acquiring each image for a given slice position at the same distance to the ECG trigger. However, this assumption may breakdown for individual frames in the case of mis-triggering, which can have different causes and is a common phenomenon especially if the patient is pharmacologically stressed during the exam. Mis-triggering occurs when an incorrect trigger event in the detected trigger events is used for the image acquisition. Frames impacted by mis-triggering may display any cardiac phase different than the rest of the dynamic series, which poses a challenge to motion compensation, both in the context of regularized reconstructions and/or for post-processing such as quantitative perfusion MRI.

Thus, the task at hand is to identify and exclude frames impacted by mis-triggering, ideally based only on ECG acquisition timestamps, because reconstructed image data, on which the different cardiac phases would be obvious, may not be available before a regularized reconstruction or further post-processing is executed.

Different methods exist to include motion information into the reconstruction, i.e. implicitly, e.g. assuming a "low-rank" periodicity, or explicitly, e.g. in the form of motion fields. While cardiac motion is periodic (e.g. in cine imaging), intermittent variations in cardiac contraction states across a dynamic acquisition due to mis-triggering are not periodic, and thus no a priori assumption on the motion can be made, which challenges approaches assuming periodicity.

Explicit motion estimation and correction algorithms are usually optimized for tackling respiratory motion, with cardiac motion (deformation) manifesting at a smaller spatial scale. Optimizing an algorithm to simultaneously estimate motion at different scales is challenging, because a priori assumptions on the spatial scale of the motion are made implicitly by controlling hyperparameters such as the smoothness of the resulting motion fields. And even if there were motion estimation or compensation algorithms that can handle respiratory and extreme cardiac motion at the same time, correcting cardiac motion in practice means warping e.g. a systolic into a diastolic frame. Different cardiac contraction states, however, represent different physiological states of tissue perfusion and blood volume, so that a series containing a mix of both is ultimately not meaningful in the context of a perfusion analysis.

Rejection of mis-triggered data before final reconstruction and/or additional post-processing could in some situations be based on already reconstructed images, e.g. preliminary reconstructions or motion fields. Classification of cardiac phases with the purpose of rejecting mis-triggered data in an image series is, however, not straightforward, and training a neural network would need large amounts of training data. The latter problem for a neural network-based approach would also apply for the purpose of rejecting mis-triggered data using only the ECG trace.

Accordingly, a need exists to overcome the above-identified problems and to provide a way to identify MR images in a series of MR images that were acquired based on a wrong trigger event based solely on the ECG trace.

SUMMARY

This need is met by the features of the embodiments as discussed herein, including in the claims.

According to a first embodiment, a method for processing a plurality of cardiac MR data sets is provided. The method comprises the step of providing the plurality of cardiac MR data sets, which were acquired over a plurality of cardiac cycles, wherein each cardiac MR data set has a corresponding timestamp at which the cardiac MR data set was acquired. Furthermore, each of the cardiac MR data sets was acquired based on a trigger event triggering the acquisition of the corresponding cardiac MR data set. Furthermore, a series of time differences between the acquisitions of the cardiac MR data sets is determined based on the timestamps. In the series of time differences, a default time difference is determined representing the time difference between two consecutive cardiac MR data sets, which were acquired using correct trigger events present in the trigger events. Furthermore, in the time differences, at least one pair of incorrect time differences is determined in the series of time differences, wherein each incorrect time difference represents the time difference between two consecutive MR data sets, in which at least one MR data set from the 2 consecutive MR data sets was acquired using an incorrect trigger event present in the trigger events. Furthermore, approved MR data sets comprising only cardiac MR data sets from the plurality of cardiac MR data sets are determined, which were acquired using the correct trigger event based on the at least one pair of incorrect time differences. The approved MR data sets can then be further processed.

It was found that the series of time differences, especially the pair of incorrect time differences, can form a basis to identify MR data sets, which were acquired based on an incorrect trigger event. A missed trigger or an incorrect trigger leads to a specific pattern in the temporal distance between the acquisition of consecutive or successive MR data sets. It was especially found that MR data sets, which are affected by an incorrect trigger event, are encapsulated by a pair of incorrect time differences. This can be interpreted as corresponding to the fact that the image acquisition enters the wrong trigger cycle and then exits the wrong trigger cycle.

For determining the approved MR data sets, which correspond to the data sets which were acquired based on the correct trigger event, it is possible to determine, in the plurality of cardiac MR data sets, first MR data sets that were acquired between the at least one pair of incorrect time differences. Furthermore, the approved MR data set is then determined while excluding the first MR data sets from the plurality of cardiac MR data sets. The first MR data sets correspond to the data sets, which were acquired between missed trigger events. Accordingly, the images generated from the first MR data sets might have another cardiac phase compared to the approved MR data sets, so that these images and data sets can be excluded. All the MR data sets acquired after entering the wrong trigger cycle, and until exiting the wrong trigger cycle, are removed.

The method can further comprise the step of determining, based on the timestamps, for the at least one pair of time differences, a time interval between the acquisition of cardiac MR data sets having incorrect time differences. The cardiac MR data sets that were acquired between the at least one pair of incorrect time differences is only confirmed as belonging to the first MR data sets if the time interval is smaller than a threshold value. When the image acquisition enters a wrong trigger cycle, it can be assumed that within a certain time the image acquisition returns to the correct trigger event. Accordingly, images are only excluded when the image acquisition in the time interval between the pair of time differences is smaller than a defined number, by way of example a number smaller than <10 acquisitions, smaller than 7 acquisitions, smaller than 5 acquisitions, smaller than any number between 4 and 7 acquisitions, etc.

The step of determining the default time difference can comprise the step of determining an average time difference in the series of time differences, and the default time difference is then determined based on the average time difference. The default time difference corresponding to the time difference occurring between two correctly identified trigger events is assumed to be present in the majority of cases of the acquired MR data sets. Accordingly, the default time difference will be close to the average time difference.

Furthermore, it is possible to carry out a clustering step in which the series of time difference is clustered, and the default time difference is determined based on the clustering based on an assumption that the cluster having the highest number of time differences is used for determining the default time difference. Here, again it is assumed that most of the acquired MR images are acquired based on the correct trigger event so that the clustering helps to identify the default time difference. If the acquisition conditions are very poor and it is hardly possible to identify the correct trigger event, the acquired MR image data will likely not provide fruitful results. Only when the major part of the cardiac MR data sets was acquired based on the correctly identified trigger events does the data provide a useful basis for a further processing.

Additionally, it is possible to determine integer multiples of the default time difference, and the cardiac MR data sets having a time difference in the series of time differences corresponding to integer multiples of the default time difference are confirmed as belonging to the approved MR data sets. It is assumed that the trigger events occur in a regular pattern, and it might be possible that one or two trigger events were missed for the image acquisition, however the image acquisition is based on the correct trigger events. Accordingly, data sets that were acquired corresponding to an integer multiple of correct trigger events are considered as belonging to the approved MR data sets even though the time difference is larger than the default time difference.

Furthermore, it is possible to identify single time differences in the series of time differences that are located at a beginning or at an end of an acquisition of the cardiac MR data sets and which differ from the default time difference by more than a threshold. The cardiac MR data sets belonging to the identified single time differences are excluded when determining the approved MR data sets. At the beginning of the acquisition, it is also possible that the acquisition is started with an incorrect trigger event and, after a while, the correct trigger event is used. Here, no pair of incorrect time differences can be detected, but the acquisition starts with an incorrect trigger event or finishes with an incorrect trigger event. The MR data sets belonging to those single time differences are also excluded for the further processing of the MR data sets.

The plurality of cardiac MR data sets can contain a number of cardiac MR images, but may also contain a number of cardiac MR raw data sets. Accordingly, it is not absolutely necessary to do an image reconstruction, and the above-mentioned analysis might only be carried out on the raw data sets as only the timestamp is needed from the different data sets.

In an embodiment, each time difference in the at least one pair of incorrect time differences has a time period larger than a time period of the default time difference. This means that the entering and exiting of the incorrect trigger events leads to a prolonged time distance between the acquisition of two consecutive MR data sets. The processing of the approved MR data sets can contain the step of determining a perfusion parameter using the approved MR data sets.

According to a further embodiment, a processing unit that is configured to process the cardiac MR data sets is provided as indicated above. Additionally, a computer program comprising program code is provided that, when executed by a processing unit, cause the processing unit to perform any of the methods as described herein.

Furthermore, a carrier is provided comprising the computer program, wherein the carrier is one of an electronic signal, optical signal, radio signal, or computer readable storage medium.

BRIEF DESCRIPTION OF THE DRAWINGS

The foregoing and additional features and effects of the application will become apparent from the following detailed description, when read in conjunction with the accompanying drawings in which like reference numerals refer to like elements.

DETAILED DESCRIPTION OF THE DISCLOSURE

In the following, embodiments of the disclosure will be described in detail with reference to the accompanying drawings. It is to be understood the following description of embodiments is not to be taken in a limiting sense. The scope of the disclosure is not intended to be limited by the embodiments described hereinafter or by the drawings, which are to be illustrative.

The drawings are to be regarded as being schematic representations, and elements illustrated in the drawings are not necessarily shown to scale. Rather, the various elements are represented such that their function and general purpose becomes apparent to a person skilled in the art. Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

Figure 1:
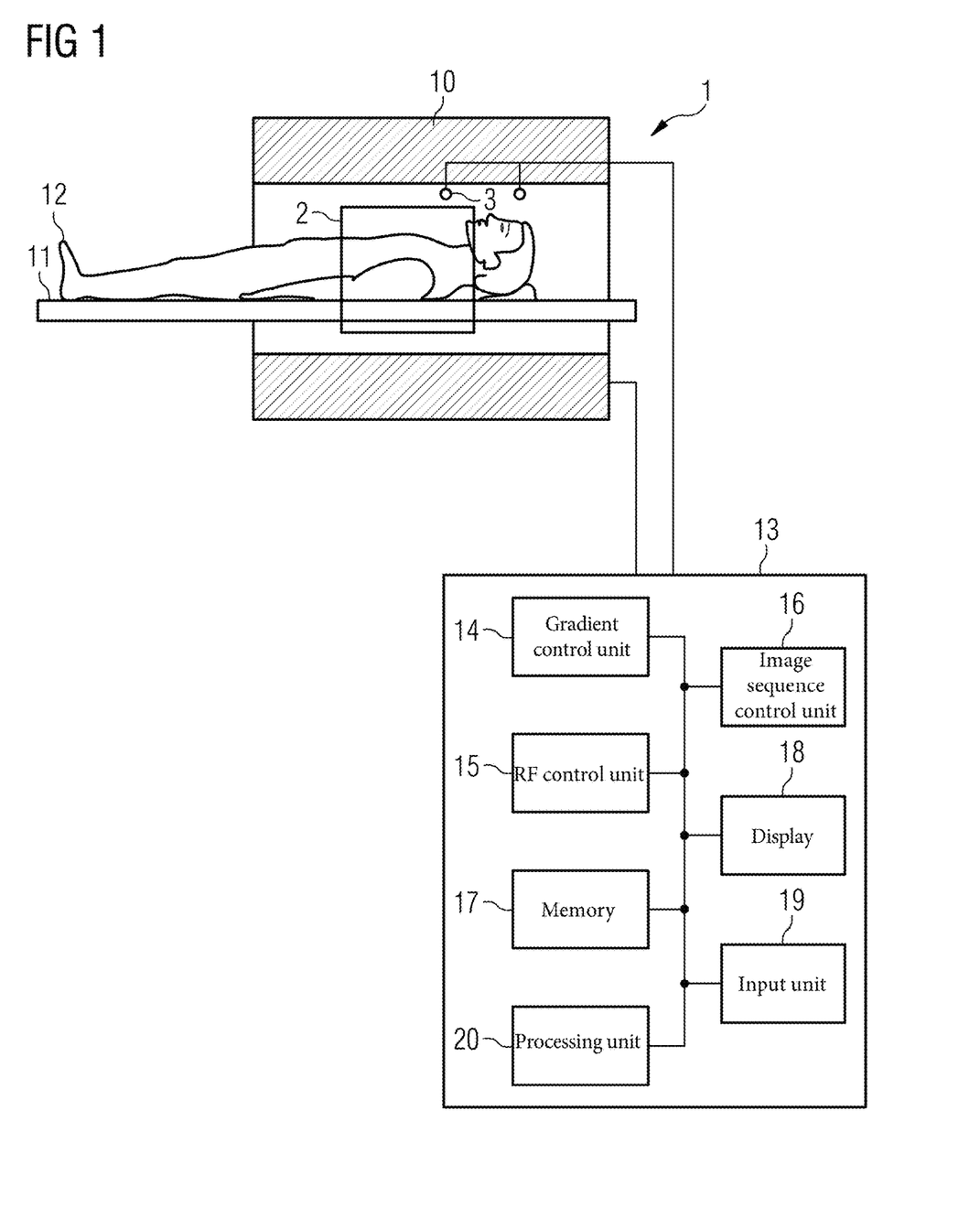
FIG. 1 illustrates a schematic view of an example MR system with which MR images of the heart can be generated and processed in such a way that cardiac MR data sets acquired with an incorrect trigger event are identified in an efficient way, in accordance with one or more embodiments of the present disclosure.

FIG. 1 shows a schematic view of an MR system 1, which compromises a magnet 10 (also referred to as a main magnet or magnetic assembly) configured to generate a polarization field B0. An object under examination 12 lying on a table 11 is moved into the center of the MR system 1 where MR signals after RF excitation can be detected by receiving coils 2, which can comprise different coil sections wherein each coil section is associated with a corresponding detection channel 3. By applying RF pulses and magnetic field gradients, the nuclear spins in the object 12 and especially in the part located in the receiving coil 2 (here the heart) are excited and location coded, and the currents induced by the relaxation can be detected. The way in which MR images are generated and how the MR signals are detected using a sequence of RF pulses and the sequence of magnetic field gradients are known in the art so that a detailed explanation thereof is omitted.

The MR system comprises a control module 13 (also referred to herein as a controller or control circuitry), which is used for controlling the MR system. The control module 13 comprises a gradient control unit 14 (also referred to herein as a gradient controller or gradient control circuitry) for controlling and switching the magnetic field gradients, an RF control unit 15 (also referred to herein as a RF controller or RF control circuitry) for controlling and generating the RF pulses for the imaging sequences. An image sequence control unit 16 (also referred to herein as an image sequence controller or image sequence gradient control circuitry) is provided that controls the sequence of the applied RF pulses and magnetic field gradients, and thus controls the gradient control unit 14 and the RF control unit 15. In a memory 17, computer programs needed for operating the MR system and the imaging sequences necessary for generating the MR images may be stored together with the generated MR images. The generated MR images may be displayed on a display 18, wherein an input unit 19 (also referred to herein as an input or a user interface) is provided used by a user of the MR system to control the functioning of the MR system. A processing unit 20 (also referred to herein as a processor or processing circuitry) can coordinate the operation of the different functional units shown in FIG. 1 and may comprise one or more processors that can carry out instructions stored on the memory 17. The memory 17 may include program code to be executed by the processing unit 20. The processing unit 20 may, based on the detected images, reconstruct MR images.

The processing unit 20 may, as discussed below, process a set of cardiac MR data in such a way that incorrect trigger events or missed triggers are identified in a reliable and effective way.

The embodiments as discussed herein provide a solution to solve the problem of rejecting mis-triggered data in cardiac MR data sets prior to reconstruction of any image data by analyzing logged trigger events and identifying a signature of mis-triggered data, which is specific to cardiac perfusion MR. This can be applied for both (pharmacological) stress and rest perfusion data. In an embodiment, the method discussed below may be applied in dynamic perfusion examinations, however it might be applied to any other cardiac MR image in which several MR data sets are acquired over different cardiac cycles.

Figure 2:
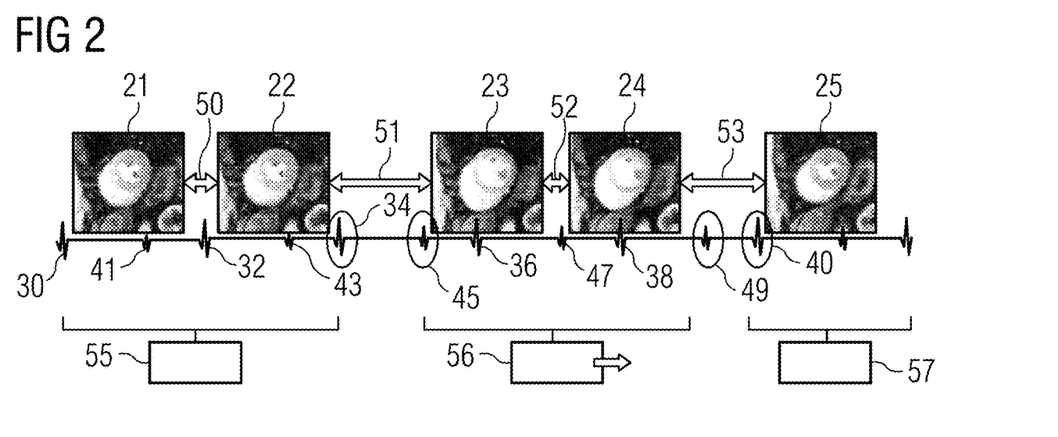
FIG. 2 illustrates a schematic view of an example interplay of correct and incorrect trigger events perturbing a cardiac imaging sequence, in accordance with one or more embodiments of the present disclosure.

FIG. 2 shows in more detail the interplay of correct and incorrect ECG trigger events, which can perturb a dynamic cardiac magnetic resonance perfusion examination. The data points and MR data sets to be rejected may be identified by identifying prolonged pairs in the time series of differences between successive acquisition times. For brevity, only one slice position is indicated per RR interval.

FIG. 2 shows how several data MR data sets 21 to 25 are acquired based on an ECG trigger signal of the heart. The R-wave in the ECG signal is shown by reference numerals 30, 32, 34, 36, 38 and 40, and plays the role of the correct trigger event. However, especially in the field of magnetic resonance imaging, the ECG signal is perturbed by artifactual trigger events such as the events 41, 43, 45, 47, and 49 as shown in FIG. 2. During the acquisition of an image, a trigger lock time is present, in which no trigger event is detected, and in which no trigger event can trigger the acquisition of the next MR image. In the example shown in FIG. 2, the system misses the correct trigger event 34, and the next data acquisition is triggered based on trigger event 45, which is an incorrect trigger. In view of the trigger lock time, the correct triggers 36 and 38 are not detected. In the example shown, the system then misses the trigger event 49, which is again an artifactual trigger and the next image is acquired based on a correct trigger 40. Images 21, 22, and 25 are images, which are acquired in the correct cardiac phase (the systole) as shown by reference numerals 55 and 57, whereas images 23 and 24 are acquired in the wrong cardiac phase, by way of example in the diastole compared to the correct cardiac phase the systole.

FIG. 2 further shows that the time difference between the acquisition of the images varies in dependence of whether a correct or wrong trigger event is used. As can be deduced from FIG. 2, the time difference 50 is a correctly-identified time difference and corresponds to a default time difference. The following time difference is a prolonged time difference 51 followed by another time difference 52, which seems to be in the same range as the time difference 50. However, the corresponding images are acquired in the wrong cardiac phase. When the system returns to the correct trigger events, another prolonged time difference 53 is present.

Accordingly as shown in FIG. 2, a missed trigger leads to a specific pattern in the temporal distance between the acquisition of successive dynamic MR data sets. While a trigger lock prevents detection of triggers during image acquisition, wherein only one slice position is shown in FIG. 1 for simplicity, artifactual triggers due to disturbances on the ECG trace may be accepted after a correct R-wave trigger is missed, pushing the trigger period into a shifted cycle until the artifactual trigger itself is missed. Accordingly, dynamic image acquisitions affected by missed trigger events are encapsulated by a pair of prolonged distances in time to the following acquisition, which corresponds to entering and exiting the shifted artifactual triggering cycle. Accordingly, by detecting a pair of incorrect time differences, here the time differences 51 and 53, it is possible to identify MR data sets that were acquired based on an incorrect or missed trigger event, even though the time difference itself between missed triggers, here the time difference 52, seems to be similar to the time difference 50.

Accordingly, the MR data sets 23 and 24 can be detected using the following procedure:

In step number 1, multiple MRI images of one or more slice-positions are acquired as a dynamic series, with the acquisition of each frame being triggered by an ECG trigger signal or an alternative cardiac triggering device. Furthermore, for each image data set, the corresponding acquisition timestamp is determined and recorded.

Figure 3:
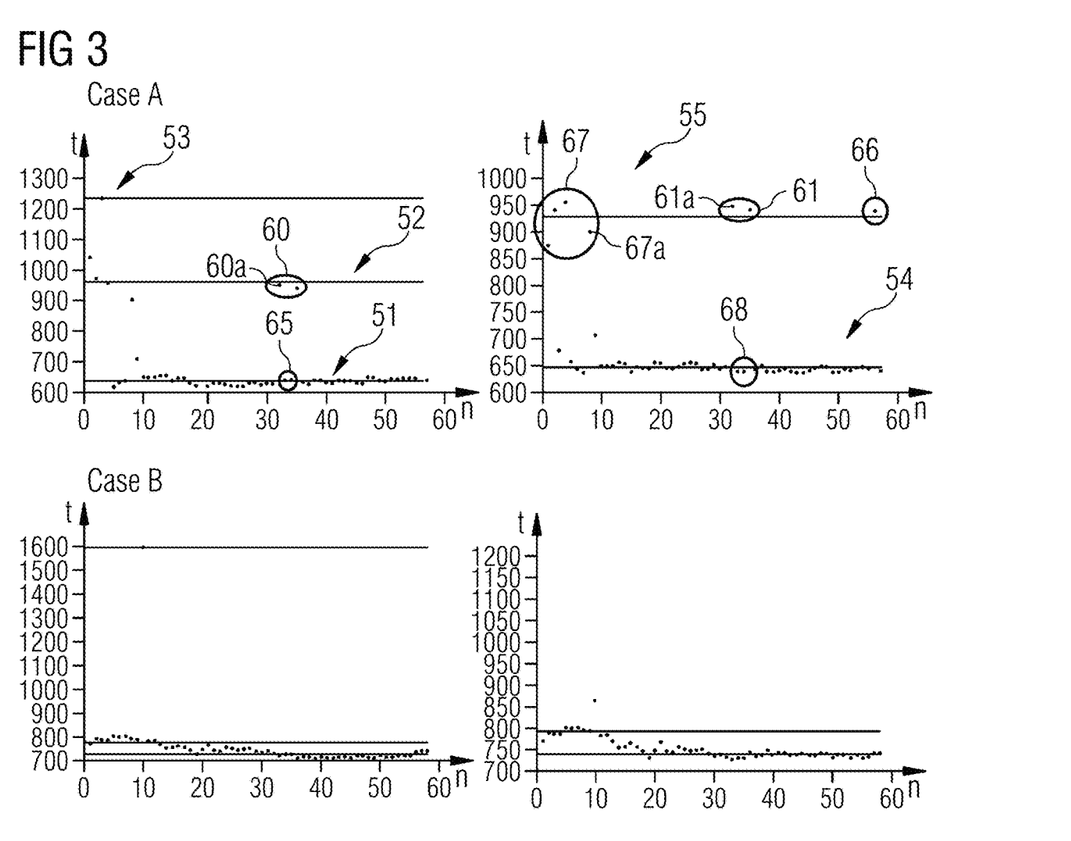
FIG. 3 illustrates different example situations of how time differences between consecutive cardiac acquisitions can be used to identify incorrect trigger events, in accordance with one or more embodiments of the present disclosure.

In a second step, the following processing can be carried out either before reconstruction of the image data, by way of example for temporarily regularized reconstructions or before further post-processing the acquired images, by way of example for an absolute quantification of the flow:

In step 2.a), a time series of the differences between the acquisition timestamps is determined. FIG. 3 shows different cases wherein the graphs in FIG. 3 show the number of image acquisitions N and the corresponding time differences in milliseconds.

In step 2.b), an average, correct trigger interval has to be found, i.e. the correct RR trigger interval in this scenario. This may be obtained via autocorrelation or by clustering the time series into different groups, such as three groups using clustering methods such as Jenks Clustering for instance. It is possible to use a clustering into three groups for the robustness against actual ectopic short heartbeats and full multi-heartbeat pauses.

In step 2.c), multiples of the correct trigger interval are eliminated in the time series, by way of example by taking a two-sided modulus. In FIG. 3, the upper left side shows the time differences for the correct trigger interval, which is slightly larger than 600 ms where also a time difference of more than 1200 ms is detected. This is double of the correct trigger interval, but as the correct trigger was used the data which were acquired with a time difference of the double correct trigger interval should not be rejected.

In step 2.d), a clustering of the time series created in step 2.c) is carried out, wherein a clustering into two groups might be used. In step 2.e), the smaller cluster is identified as being the cluster of the incorrect triggers. This step is based on the assumption that most of the times the correct trigger was identified. If this is not the case, the complete image data set may not be appropriate for further processing. The identification of the smaller cluster could be carried out under the condition that, by way of example, the difference between the cluster means is larger than a certain time threshold set, such as 150 ms for example, and the size of the smaller cluster is such that it contains less than 30% for example, or any other suitable threshold number of the complete data.

Referring to FIG. 3, a first situation (case A) is shown in the upper two graphs, which is called the first case in the following, where at the beginning three clusters of time differences were identified: cluster 51, 52, and 53. As it was found that cluster 53 corresponds to a multiple of the cluster 50, the time difference occurring in a cluster 53 is assumed to be a correct time difference, namely a multiple of the correct trigger distance. Cluster 52 is a prolonged trigger interval and is not a multiple of the correct trigger interval, so it can be determined that the corresponding images were acquired at the wrong cardiac cycle.

The same is true for the upper right part of FIG. 3, which shows a cluster 54 and a cluster 55. Cluster 54 represents the correct trigger interval, whereas cluster 55 represents the wrong trigger interval.

In the next step 2.1), it is necessary to identify pairs of missed triggers, as the pair 60 shown in the left upper part and the pair 61 shown in the upper right part of FIG. 3. Referring back to FIG. 2, these 2 data points could correspond to the prolonged time difference 51 and 53 shown in FIG. 2. Accordingly, it is necessary to exclude the data acquisitions between these two time differences. Accordingly, the time differences occurring between these two pairs here including the first end excluding the second partner of the pair, the time differences 65 and 60a, or 68 and 61a, and the corresponding MR data sets, have to be identified. Even though the time differences 65 and 68 seem to be based on the correct trigger interval, they belong to the wrong cardiac phase or cycle, so that it is necessary to exclude those data sets from the image processing. The identification of the pair of time differences 60 or 61 shown in FIG. 3 helps to identify the time differences 65 and 68 occurring between the corresponding pair. The image data acquisitions belonging to the time differences 65 and 60a, as well as 68 and 61a, now should be excluded from the further processing.

A possible exception to the encapsulation between pairs represents the case in which one of the two missed trigger events is outside of the dynamic image acquisition, accordingly at the end or at the start of the image acquisition. As a consequence, it is advisable to also exclude image acquisitions before/after a single missed trigger at the beginning/end of the series of acquisitions. Referring to FIG. 3, this means that a single missed trigger 66 occurs at the end of the acquisition. Based on the assumption that the images after this trigger are based on the wrong cardiac cycle, all the MR data sets occurring after this single time difference are excluded.

For the determination of the pairs of incorrect time differences, one can further assume that the distance between incorrect pairs should not be larger than a certain number of successive wrong triggers, the number being any suitable number such as e.g. a number between 4 and 10, a number between 4 and 6, etc. Accordingly, it can be assumed that the data points 67a and 61a shown in FIG. 3 do not correspond to a single pair of incorrect time differences, as the distance between those image acquisitions is too large.

Summarizing, in step 2.g), for each pair found in step 2.f, accordingly for each pair 60 or 61 shown in FIG. 3, the data acquisitions in between those missed triggers are excluded from the further processing. At the end, approved MR data sets are determined which contain all the MR data sets which were acquired based on the correct trigger interval or at least on a multiple of the correct trigger interval. The data sets which were acquired between the pair of incorrect time differences can be called first data sets, which are excluded from the further processing. In a further third step, it is then possible to reconstruct or process the image data, namely the approved MR data sets, after the data acquired in the wrong cardiac phase was excluded as discussed above. In a further optional step, it is possible to reconstruct and display also the rejected data separately to avoid a loss of any diagnostic information.

Case B as shown in FIG. 3 shows another situation where only a single missed trigger is detected, which is however a multiple of the correct trigger interval. Accordingly, no significant cluster difference occurs and none of the data has to be rejected. The same is true for the lower right part of FIG. 3.

Figure 4:
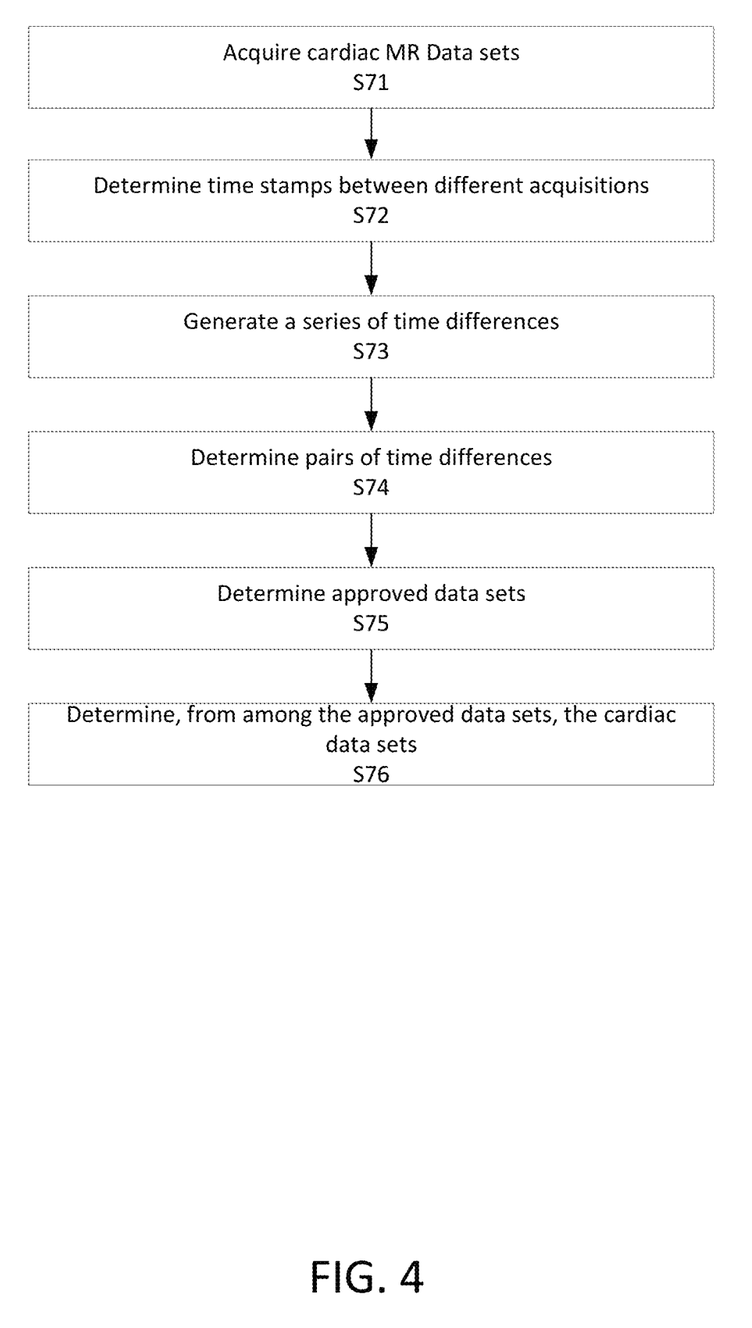
FIG. 4 illustrates a schematic view of an example flow comprising steps carried out for identifying MR data sets that were acquired based on incorrect trigger events, in accordance with one or more embodiments of the present disclosure.

FIG. 4 summarizes some of the steps carried out in the above-discussed identification of MR data sets, which were acquired at the wrong cardiac phase of the cycle.

In a first step, the cardiac MR data sets are provided, which were acquired over several cardiac cycles (step S71). Those data set comprise data sets, which were acquired based on the correct trigger event and based on an incorrect trigger event. In step S72, time differences are determined between the different acquisitions based on the timestamps of the acquisitions. Accordingly, a series of time differences is generated. In a further step, in the series of time differences, a default time difference is determined representing the time difference between two consecutive cardiac MR data sets, which were acquired using a correct trigger event (step S73). As discussed above, this determination of the default time difference can be based on autocorrelation or clustering of the time series as it is assumed that the major part of the images were acquired with the correct trigger event. If it is detected that one cluster is not much larger than the other cluster, it is also possible to discard the complete data set, as it might be assumed that the complete image acquisition cannot provide diagnostic relevant information. Based on the default time difference, it is also possible to determine pairs of incorrect time differences in step S74, as discussed above in connection with FIG. 3, e.g. the pairs of time differences 61 or 60. Based on this pair of incorrect time differences, it is possible to determine the approved data sets in step S75, which only contain the cardiac MR data sets, and which were acquired based on a correct trigger event. In step S76, the approved data set can be further processed, meaning that an image reconstruction may be carried out or the image data or further processed such as the determination of a perfusion parameter.

Summarizing, the proposed approach identifies cardiac MR perfusion data affected by missed or incorrect triggers by using a specific signature in the acquisition timestamp. The above described method increases the sharpness and the fidelity of motion-compensated image series after temporal regularization and/or before the post-processing, such as the absolute perfusion quantification. Furthermore, any a priori assumptions on the nature of the underlying cardiac motion is avoided. Further, it is not necessary to estimate and/or correct the motion between different cardiac contraction states in addition to the respiratory motion. Moreover, there is no need to reconstruct image data before the data to be rejected is identified. This is possible as only the time difference is needed between the acquisitions. Finally, no user interaction or ground truth training data or a neural network is required. An efficient way is thus provided to remove MR data sets acquired in a series of MR images, which were acquired in a wrong cardiac phase.

The various components described herein may be referred to as "units" or "modules." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units or devices, as applicable and relevant, may alternatively be referred to herein as "circuitry," "controllers," "processors," or "processing circuitry," or alternatively as noted herein.

What is claimed is:

1. A method, comprising:
   acquiring, via execution of a cardiac imaging sequence performed via a magnetic resonance (MR) device, a plurality of cardiac MR data sets over a plurality of cardiac cycles, each cardiac MR data set from among the plurality of cardiac MR data sets having a corresponding time stamp at which the respective cardiac MR data set was acquired, and each of the plurality of cardiac MR data sets being acquired in response to a respective trigger event;
   calculating a series of time differences between acquisitions of the plurality of cardiac MR data sets based on the time stamps;
   calculating, in the series of time differences, a first time difference representing a time difference between two consecutive cardiac MR data sets that were acquired using electrocardiogram (ECG) trigger events that correspond to ECG trigger signals;
   calculating, in the series of time differences, a pair of second time differences, each second time difference representing a time difference between two consecutive MR data sets in which at least one MR data set from the two consecutive MR data sets was acquired using an artifactual trigger event;
   calculating, based on the pair of second time differences and prior to performing image reconstruction, qualifying cardiac MR data sets comprising only cardiac MR data sets from among the plurality of cardiac MR data sets that were acquired using a respective ECG trigger event; and
   selectively reconstructing one or more cardiac MR images from the plurality of cardiac MR data sets by processing the qualifying cardiac MR data sets to reconstruct the one or more cardiac MR images.

2. The method of claim 1, wherein the calculating the qualifying cardiac MR data sets comprises:
   calculating, in the plurality of cardiac MR data sets, first cardiac MR data sets that were acquired between the pair of second time differences; and
   calculating the qualifying cardiac MR data sets by excluding the first cardiac MR data sets from the plurality of cardiac MR data sets.

3. The method of claim 2, further comprising:
   calculating, based on the time stamps and for the pair of second time differences, a time interval between the acquisition of cardiac MR data sets having second time differences; and
   calculating cardiac MR data sets acquired between the pair of second time differences as belonging to the first cardiac MR data sets when the time interval is smaller than a threshold value.

4. The method of claim 3, wherein the calculating the cardiac MR data sets acquired between the pair of second time differences comprises calculating the cardiac MR data sets acquired between the pair of second time differences as belonging to the first cardiac MR data sets when the time interval is smaller than a threshold value corresponding to a number of consecutive cardiac MR data sets from the plurality of cardiac MR data sets, the number being an integer that is smaller than 10.

5. The method of claim 3, wherein the calculating the cardiac MR data sets acquired between the pair of second time differences comprises calculating the cardiac MR data sets acquired between the pair of second time differences as belonging to the first cardiac MR data sets when the time interval is smaller than a threshold value corresponding to a number of consecutive cardiac MR data sets from the plurality of cardiac MR data sets, the number being an integer that is smaller than 7.

6. The method of claim 3, wherein the calculating the cardiac MR data sets acquired between the pair of second time differences comprises calculating the cardiac MR data sets acquired between the pair of second time differences as belonging to the first cardiac MR data sets when the time interval is smaller than a threshold value corresponding to a number of consecutive cardiac MR data sets from the plurality of cardiac MR data sets, the number being an integer that is smaller than 5.

7. The method of claim 1, wherein the first time difference is determined based on an average time difference in the series of time differences.

8. The method of claim 1, further comprising:
calculating integer multiples of the first time difference,
wherein cardiac MR data sets from among the plurality of cardiac MR data sets having a time difference in the series of time differences corresponding to integer multiples of the first time difference are calculated as belonging to the qualifying cardiac MR data sets.

9. The method of claim 1, further comprising:
clustering the series of time differences,
wherein the first time difference is calculating based on the clustering by using a largest cluster of time differences for calculating the first time difference.

10. The method of claim 1, further comprising:
identifying single time differences in the series of time differences that are located at a beginning or at an end of the cardiac MR data sets and differ from the first time difference in excess of a threshold value,
wherein the cardiac MR data sets identified with the identified single time differences are excluded to determine the qualifying MR data sets.

11. The method of claim 1, wherein the acquiring the plurality of cardiac MR data sets comprises acquiring, as the plurality of cardiac MR data sets, one or more cardiac MR images.

12. The method of claim 1, wherein the acquiring the plurality of cardiac MR data sets comprises acquiring, as the plurality of cardiac MR data sets, one or more cardiac MR raw data sets.

13. The method of claim 2, wherein the calculating, in the plurality of cardiac MR data sets, the first cardiac MR data sets that were acquired between the pair of second time differences as each time difference in the pair of second time differences having a time period larger than a time period of the first time difference.

14. The method of claim 1, wherein the processing the qualifying cardiac MR data sets comprises reconstructing a dynamic image series using a temporal regularization term.

15. The method of claim 1, wherein the processing the qualifying cardiac MR data sets further comprises calculating a perfusion parameter based on the qualifying cardiac MR data sets.

16. A controller, comprising:
processing circuitry configured to:
acquire, via execution of a cardiac imaging sequence performed via a magnetic resonance (MR) device, a plurality of cardiac magnetic resonance (MR) data sets over a plurality of cardiac cycles, each cardiac MR data set from among the plurality of cardiac MR data sets having a corresponding time stamp at which the respective cardiac MR data set was acquired, and each of the plurality of cardiac MR data sets being acquired in response to a respective trigger event;
calculate a series of time differences between acquisitions of the cardiac MR data sets based on the time stamps;
calculate, in the series of time differences, a first time difference representing the time difference between two consecutive cardiac MR data sets that were acquired using electrocardiogram (ECG) trigger events that correspond to ECG trigger signals;
calculate, in the series of time differences, a pair of second time differences, each second time difference representing a time difference between two consecutive MR data sets in which at least one MR data set from the two consecutive MR data sets was acquired using an artifactual trigger event;
calculate, based on the pair of second time differences, qualifying MR data sets comprising only cardiac MR data sets from the plurality of cardiac MR data sets that were acquired using a respective correct trigger event; and
selectively reconstruct one or more cardiac MR images from the plurality of cardiac MR data sets by processing the qualifying MR data sets to reconstruct one or more cardiac MR images; and
a display configured to present the reconstructed one or more cardiac MR images.

17. A non-transitory computer-readable medium having instructions stored thereon that, when executed by a processor of a magnetic resonance (MR) system, cause the MR system to:
acquire, via execution of a cardiac imagine sequence performed via a magnetic resonance (MR) device, a plurality of cardiac MR data sets over a plurality of cardiac cycles, each cardiac MR data set from among the plurality of cardiac MR data sets having a corresponding time stamp at which the respective cardiac MR data set was acquired, and each of the plurality of cardiac MR data sets being acquired in response to a respective trigger event;
calculate a series of time differences between acquisitions of the cardiac MR data sets based on the time stamps;
calculate, in the series of time differences, a first time difference representing the time difference between two consecutive cardiac MR data sets that were acquired using electrocardiogram (ECG) trigger events that correspond to ECG trigger signals;
calculate, in the series of time differences, a pair of second time differences, each second time difference representing a time difference between two consecutive MR data sets in which at least one MR data set from the two consecutive MR data sets was acquired using an artifactual trigger event;

calculate, based on the pair of second time differences, qualifying MR data sets comprising only cardiac MR data sets from the plurality of cardiac MR data sets that were acquired using a respective correct trigger event; and selectively reconstruct one or more cardiac MR images from the plurality of cardiac MR data sets by processing the qualifying MR data sets to reconstruct one or more cardiac MR images.

* * * * *